United States Patent [19]

Heitmann

[11] Patent Number: 4,639,592
[45] Date of Patent: Jan. 27, 1987

[54] CIGARETTE TESTING APPARATUS

[75] Inventor: Uwe Heitmann, Hamburg, Fed. Rep. of Germany

[73] Assignee: Hauni-Werke Körber & Co. Kg., Hamburg, Fed. Rep. of Germany

[21] Appl. No.: 620,578

[22] Filed: Jun. 14, 1984

[30] Foreign Application Priority Data

Jun. 14, 1983 [DE] Fed. Rep. of Germany ....... 3321408

[51] Int. Cl.$^4$ ............................................. G01N 21/88
[52] U.S. Cl. ................................. 250/223 B; 250/572; 356/240
[58] Field of Search .................... 356/237, 239, 240; 250/223 B, 214 RC, 572; 209/535, 536, 540

[56] References Cited

U.S. PATENT DOCUMENTS 4,483,615  11/1984  Bieringer et al. ................... 250/572

Primary Examiner—Gene Wan
Attorney, Agent, or Firm—Peter K. Kontler

[57] ABSTRACT

A cigarette testing apparatus wherein a single layer of cigarettes is transported sideways in the flutes of two conveyors one of which exposes a first half of the wrapper of each cigarette thereon from the one to the other end of the cigarette and the other of which exposes the remaining half of the wrapper. A first optoelectrical scanning system monitors the first half of the wrapper of each cigarette on the first conveyor for the presence or absence of defects, and a discrete second optoelectrical scanning system monitors the remaining half of the wrapper of each cigarette on the second conveyor for the presence or absence of defects. Each of the two systems can employ two discrete scanning units having light sources, mirrors and lenses which focus light from the sources upon the respective halves of the wrappers, rows of photoelectric transducers, and elements which focus reflected light upon the transducers. The outputs of the transducers are connected with an evaluating circuit which generates defect signals for segregation of defective cigarettes from the remaining cigarettes. The defects which are ascertained by the apparatus include the absence of imprints, improper application of imprints, open seams and/or holes in the wrappers, absence of filter plugs in filter cigarettes, improper application of uniting bands which secure filter plugs to plain cigarettes, bending or other types of deformation of cigarettes, the presence of smudges and/or a combination of the above.

24 Claims, 7 Drawing Figures

CIGARETTE TESTING APPARATUS

BACKGROUND OF THE INVENTION

The present invention relates to apparatus for testing cigarettes and other rod-shaped articles of the tobacco processing industry. More particularly, the invention relates to improvements in apparatus for ascertaining the presence or absence of defects at the exterior of rod-shaped articles of the tobacco processing industry, especially for detecting the presence or absence of smudges, open seams, holes and/or frayed ends, the presence or absence of imprints, improper application of imprints, the presence of absence of filter mouthpieces in filter cigarettes, cigars or cigarillos, the presence or absence of dents, flexure or bending of plain or filter cigarettes, cigars or cigarillos and/or filter rod sections, whether or not the uniting bands which connect filter mouthpieces to plain cigarettes, cigars or cigarillos are properly attached, departure of the outline of an article from round and/or a combination of such defects.

It is already known to monitor the exterior of rod-shaped articles of the tobacco processing industry while such articles form a single layer and advance sideways (namely at right angles to their respective longitudinal axes) on a testing conveyor, e.g., a fluted drum. The testing apparatus normally or often comprises optical testing means which can include a radiation source, means for focusing one or more beams of radiation upon the exterior of the article at the testing station, and means for evaluating radiation which is reflected by the exterior of the article because changes in the characteristics of radiation which is reflected by a cigarette or the like are indicative of the quality of the wrapper of such commodity. The just described conventional testing apparatus can be used to ascertain the condition of a wide variety of rod-shaped articles of the tobacco processing industry including filter rod sections, plain or filter cigarettes, cigars or cigarillos, cheroots or others.

The following description of the invention will refer primarily to filter cigarettes or plain cigarettes; however, it is to be understood that the apparatus of the present invention can be used with equal advantage for the testing of all kinds of rod-shaped articles of the tobacco processing industry.

It is customary to test successive plain or filter cigarettes after they issue from a cigarette rod making machine or in a cigarette making machine proper. Such final test is intended to allow for segregation of defective cigarettes from satisfactory cigarettes before the cigarettes are introduced into the packing machine or into storage so that defective cigarettes cannot reach the consumer. A drawback of presently known testing apparatus which are utilized for such purposes is that they cannot detect all defects which are, or are likely to be, present and which can be ascertained as a result of optical inspection of the exterior of the articles. For example, if the wrappers of cigarettes are tested by pneumatic means (which normally involves introduction of compressed air into one end of the article and monitoring the drop of pressure which is attributable to escape of testing fluid through open seams, holes or like defects in the wrapper of the article), such pneumatic testing cannot ensure the detection of all defects because a hole which happens to be sealed by a tobacco shred on by a piece of tobacco rib does not permit the escape of testing fluid even though it constitutes or can constitute a serious defect. Moreover, pneumatic testing cannot invariably lead to detection of many other types of defects which may not result in leakage of tobacco smoke through the wrapper but detract from the appearance of the product. Such defects include the presence of tobacco crumbs between those portions of wrapping material which form the customary longitudinally extending seam of a cigarette. Still further, if the articles to be tested are filter cigarettes, pneumatic testing cannot invariably reveal the quality of uniting bands which connect the filter plugs to the respective plain cigarettes. For example, a uniting band may extend partially beyond the general outline of the filter cigarette to thus detract from its appearance. Furthermore, a corner portion of a uniting band can be bent outwardly and such defect, too, cannot be detected by a pneumatic testing apparatus which is designed to establish a pressure differential between the interior and the exterior of the wrapper. Still further, pneumatic testing apparatus cannot detect dented, bent, flexed or otherwise mechanically deformed plain or filter cigarettes.

Attempts to detect the presence of defects which cannot be detected by pneumatic testing means include resort to optical testing means. Thus, it was already proposed to optically scan the exterior of the continuous cigarette rod which is turned out by a cigarette rod making machine and is thereupon subdivided into plain cigarettes of unit length or multiple unit length. A drawback of such proposal is that the optical testing apparatus cannot detect the presence of all defects which are likely to be present in the ultimate product, namely in plain or filter cigarettes of unit length or multiple unit length. This is due to the fact that many defects develop during and/or subsequent to subdivision of a continuous cigarette rod into plain cigarettes of unit length or miltiple unit length. Those defects which can arise subsequent to subdivision of the rod into discrete plain cigarettes can include holes, smudges, spots of adhesive extending outwardly beyond the seams, the absence of imprints, improperly applied imprints, improperly applied filter mouthpieces, denting, bending or flexing of articles subsequent to severing of the rod, and many others. Therefore, a production line which employs such optical testing apparatus must be equipped with additional testing apparatus which monitor the condition of the ultimate products, such as plain or filter cigarettes, in order to detect defects which are not detectable or do not exist at the time when the tobacco-containing portion of the ultimate product constitutes a coherent rod wherein a tubular wrapper surrounds a filler consisting of natural, reconstituted or substitute tobacco. On the other hand, optical testing of a cigarette rod exhibits the advantage that the entire exterior of the wrapper of the rod can be monitored upstream of the cutoff which serves to subdivide the rod into plain cigarettes of unit length or multiple unit length.

German Offenlegungsschrift No. 28 40 617 discloses an apparatus which serves for optical testing of the exterior of discrete rod-shaped products of the tobacco processing industry, particularly plain or filter cigarettes of unit length or multiple unit length. In accordance with the proposal in this German printed publication, successive cigarettes are transported individually into a testing zone and are brought to a standstill prior to beginning to rotate around their respective longitudinal axes through an angle of at least 360°. This enables the optical testing instrumentalities to inspect the entire exterior of the article at the testing station. The testing apparatus normally comprises a source of radiation, means for directing radiation against the exterior of the rotating article at the testing station, and means for monitoring changes in the characteristics of radiation upon reflection because such cahnges are, or can be considered to be, indicative of the presence of one or more defects at the exterior of the tested article. This proposal exhibits the serious drawback that the testing operation takes up a considerable amount of time because each article to be tested must be transported to a predetermined testing station, its forward progress must be interrupted, and it must be set in rotary motion about its longitudinal axis in order to make sure that the testing apparatus can examine the entire exterior of the wrapper. Furthermore, the means for rotating the article at the testing station about its longitudinal axis is likely to subject such article to pronounced mechanical stresses, especially if the rotation through and angle of at least 360° should be completed within a reasonably short interval of time. Consequently, the means for rotating the article at the testing station is likely to affect the appearance of the wrapper and/or to otherwise damage the wrapper as a result of transmission of torque thereto.

A different optical testing apparatus is disclosed in German Offenlegungsschrift No. 30 30 140. This apparatus is designed to monitor the exterior of the wrappers of cigarettes which are caused to move sideways on a suitable conveyor. The apparatus comprises means for directing light against the exterior of the article which passes through a testing zone, and a so-called linear camera is provided to evaluate the reflected radiation, i.e., the camera is designed to evaluate a strip or line of radiation which is reflected by the article at the testing location. A drawback of such proposal is that the apparatus is incapable of testing the entire exterior of the wrapper of a cigarette. Consequently, the apparatus cannot ensure the detection of any and all defects which are likely to occur in a cigarette and are apt to develop subsequent to subdivision of a continuous rod into discrete articles or are of the type which cannot be detected while the commodity which is being tested still constitutes a continuous rod. If the just discussed apparatus were to be designed to ensure adequate monitoring of the entire exterior of the wrapper of each of a series of cigarettes or the like, it would be necessary to provide means for rotating each article about its own axis, the same as described above in connection with the first-mentioned German printed publication. The disclosure of German Offenlegungsschrift No. 30 30 140 does not contain any proposal to rotate the articles about their respective axes while the articles are located at the testing station.

OBJECTS AND SUMMARY OF THE INVENTION

An object of the present invention is to provide a novel and improved apparatus which can test cigarettes and other rod-shaped articles of the tobacco processing industry at the rate at which such articles are formed in a high-speed cigarette rod making or like machine and in such a way that each and every portion of the exterior of each and every article can be accurately monitored for the presence or absence of defects.

Another object of the invention is to provide a novel and improved optical scanning apparatus for plain or filter cigarettes or other types of rod-shaped articles of the tobacco processing industry.

A further object of the invention is to provide an apparatus which can properly test the entire exterior of the wrapper of each and every rod-shaped article of the tobacco processing industry but does not necessitate the provision of means for rotating the articles about their respective axes in the course of the testing operation.

Still another object of the invention is to provide an apparatus which can detect practically all kinds of defects which can be expected to develop in or close to the wrappers of plain or filter cigarettes, cigars, cigarillos and/or filter rod sections.

A further object of the invention is to provide the apparatus with novel and improved means for scanning the exterior of the wrappers of plain or filter cigarettes or other rod-shaped articles of the tobacco processing industry.

An additional object of the invention is to provide a novel and improved method of examining the entire exterior of the wrapper of each of a short or a long series of rod-shaped articles of the tobacco processing industry for the presence or absence of smudges, open seams, holes, frayed ends as well as for the presence or absence of filter mouthpieces, the quality of the applied uniting bands, the configuration of the articles and/or any combinations of such defects in a time- and space-saving operation.

Still another object of the invention is to provide a method which ensures complete examination of the exterior of each and every article while such article advances in a production line from the locus of making toward a processing station, for example, between a cigarette rod making and a cigarette packing machine.

A further object of the invention is to provide the above-outlined apparatus with novel and improved means for directing radiation against as well as for directing reflected radiation from tested articles.

An additional object of the invention is to provide a testing apparatus which can be installed in existing production lines for rod-shaped articles of the tobacco processing industry as a superior substitute for heretofore utilized testing apparatus.

Another object of the invention is to provide a testing apparatus which is compact and relatively simple and is capable of detecting any and all defects that are liekly to arise not only prior to but also after subdivision of a continuous tobacco-containing or filter material-containing rod into sections of unit length or multiple unit length.

Another object of the invention is to provide an apparatus which treats the articles to be tested gently and which can furnish reliable indications regarding the condition of tested articles.

A further object of the invention is to provide an apparatus which can invariably test the entire exterior of each and every article to be tested.

A further object of the invention is to provide the apparatus with novel and improved means for transporting the articles in such a way that the entire exterior of each and every article is available for monitoring of the condition of the wrapper and/or other parts of the article.

One feature of the invention resides in the provision of an apparatus for ascertaining the presence or absence of defects at the exterior of rod-shaped articles of the tobacco processing industry. The apparatus comprises means for transporting a series of articles in a predetermined direction at right angles to the axes of the articles and along successive portions (testing stations) of a predetermined path. The arrangement is such that, in each portion of the path, a different section of the exterior of the article becomes exposed. Such apparatus further comprises discrete scanning means for each portion of the path, and each scanning means comprises means for monitoring the respective section of the exterior of the article in the corresponding portion of the path. Thus, if a first portion of the path allows for exposure of one-half of the exterior of the wrapper of a cigarette or the like, and a second portion of the same path allows for exposure of the other half of the wrapper of each article, the scanning means of such apparatus can examine the entire exterior of the wrapper of each article for the presence of a wide variety of different or similar defects including smudges, absence of filter plugs in filter cigarettes, improper application of uniting bands in filter cigarettes, open seams, holes, frayed ends, the absence of imprints, improper application of imprints and/or many others.

The transporting means preferably includes means for conveying the series of articles in the form of a single layer, and each scanning means can comprise at least one optical scanning unit. Each such unit can include a source of radiation, means for directing radiation from the source against the respective section of the exterior of the article in the corresponding portion of the path whereby the characteristics of such radiation change in response to impingement upon a defective section of the exterior of the article in the corresponding portion of the path, and means for monitoring such changes in the characteristics of radiation. Each radiation source can constitute a light source, and the monitoring means of each unit can include optoelectrical transducer means.

Each of the aforementioned sections of the exterior of an article preferably extends along the full length of the corresponding article, and the monitoring means of each unit preferably includes a plurality of discrete transducers each of which is arranged to detect changes in the characteristics of radiation upon impingement of such radiation upon one of several longitudinally spaced increments of the respective section of the exterior of the article in the corresponding portion of the path. In other words, an entire row or several rows of transducers can be used in each unit so that each transducer can generate a signal denoting the characteristics of a relatively small portion of reflected radiation. In this manner, the apparatus can ascertain the exact location of a particular defect, for example, an open seam or a hole, at a given distance from the one or the other axial end of the tested article. Each of the transducers can constitute an optoelectrical transducer arranged to ascertain the characteristic of radiation which is reflected by the respective increments of the exterior of the article in the corresponding portion of the aforementioned path.

In accordance with a presently preferred embodiment of the apparatus, each scanning means comprises several optical scanning units, and each such unit can comprise a source of radiation and radiation conducting means which directs radiation issuing from the respective source against the respective section of the exterior of the article in the corresponding portion of the path at a different angle to such path. For example, each of the radiation conducting means can be arranged to direct radiation against the respective sections of the exterior of the article in the corresponding portion of the path and along the full length of such article. If each scanning means comprises a pair of scanning units, the radiation conducting means of each pair of units can be arranged to direct radiation at an angle of approximately 90° to each other. The axes of the articles in the aforementioned path are disposed in a predetermined plane which may but need not be a flat plane. The radiation directing means of each pair of units are preferably arranged to direct beams of radiation at angles of approximately 45° to such plane. The beams which are directed by the radiation directing means of each pair of units preferably intersect each other in the aforementioned plane which includes the axes of the articles in the path.

The transporting means can comprise several neighboring conveyors with a transfer zone between neighboring conveyors. Each such conveyor can constitute a rotary drum having axially parallel peripheral flutes. The conveyors include a first and second conveyor, and the aforementioned portions of the path then include first and second portions (testing stations) which are defined by the respective (first and second) conveyors. The number of transfer zones in the transporting means between the first and second conveyors is preferably an odd number (for example, one). This ensures that one of the conveyors invariably exposes that section of the exterior of the wrapper of an article which is, or is likely to be, concealed while the article travels with the other conveyor.

Each of the scanning means can comprise at least one elongated radiation source which extends at right angles to the direction of movement of articles along their path and in at least substantial parallelism with the articles in the path.

In accordance with a presently preferred embodiment of the invention, each scanning means can comprise at least one radiation source, first radiation conducting means for focusing the radiation which issues from the source upon the respective section of the exterior of the article in the corresponding portion of the path whereby such section reflects radiation, transducer means which is or are arranged to monitor the characteristics of reflected radiation, and second radiation conducting means for focusing reflected radiation upon the transducer means. The radiation conducting means can comprise optical elements, especially if the radiation source emits light. The transducer means of each scanning means can comprise a battery of transducers and the second radiation conducting means of each scanning means preferably comprises means for directing a different portion of reflected radiation against each of the transducers so that each transducer ascertains the characteristics of radiation which is reflected by one of several longitudinally spaced increments of the respective sections of the exterior in the article in the corresponding portion of the path. The radiation conducting means of each scanning means can comprise mirrors and lenses which are or can be arranged to provide for emitted and reflected radiation paths which include a common portion.

The means for monitoring the characteristics of reflected radiation can include a two-dimensional array of transducers which are located in the path of propagation of reflected radiation so that the radiation which impinges upon such an array of transducers forms an image of the corresponding article. The scanning means which employs such two-dimensional array of transducers preferably comprises radiation conducting means which is disposed in the path of propagation of reflected radiation and serves to alter at least one dimension of the image which is formed on the respective array. This is often desirable and advantageous because a small dot-shaped defect can be imaged in the array in the form of an elongated line which is much more readily detectable than a minute spot representing, for example, a small hole in the wrapper of a plain or filter cigarette.

Each of the second radiation conducting means in each of the scanning means can comprise at least one cylinder lens.

The signals which are generated by the transducers of each scanning means can be transmitted to the corresponding inputs of a common evaluating circuit which is designed to generate "defect" signals when the intensities or other characteristics of signals received from the transducers deviate appreciably from reference or threshold signals denoting the characteristics of satisfactory articles. Such "defect" signals can be used for segregation of corresponding articles from the remaining articles.

Another feature of the invention resides in the provision of a method of testing the exterior of rod-shaped articles of the tobacco processing industry. The method comprises the steps of transporting a series of successive articles sideways along a predetermined path including a first portion wherein a first section of the exterior of each article is exposed at least substantially from end to end and a second portion in which a different second section of the exterior of each article is exposed at least substantially from end to end, scanning the first sections of the exterior of successive articles in the first portion of the path for the presence or absence of defects, and scanning the second sections of the exterior of successive articles in the second portion of the path for the presence or absence of defects. Each of the scanning steps preferably includes directing beams of radiation against the respective sections of the exterior of the article in the corresponding portion of the path whereby the exterior of each article reflects the radiation and the characteristics of reflected radiation are indicative of defects, if any in the respective sections, and monitoring the characteristics of reflected radiation.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
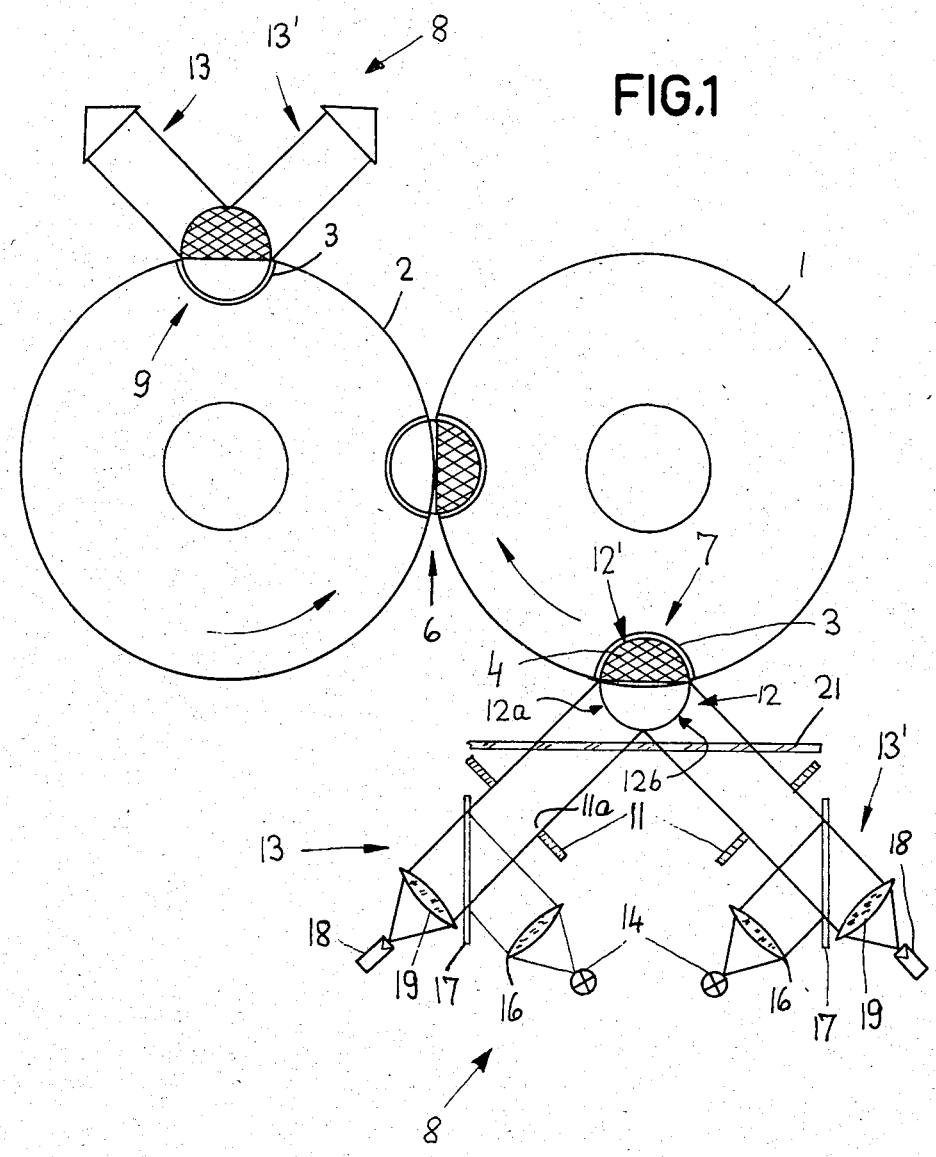
FIG. 1 is a schematic end elevational view of a cigarette testing apparatus which embodies one form of the present invention.

FIG. 1 shows an apparatus for testing a series of successive filter cigarettes 4 each of which has a tobacco containing portion or plain cigarette P (see FIG. 3) and a filter plug F. The filter plug F is attached to the plain cigarette P by a tubular wrapper which consists of so-called tipping paper and completely surrounds the filter plug as well as the adjacent end portion of the plain cigarette. The apparatus comprises transporting means including a series of successive rotary drum-shaped conveyors 1, 2 having axially parallel peripheral flutes 3 each of which is arranged to receive a portion of a cigarette 4. In other words, that portion of the cigarette which is received in a flute 3 is not exposed and, at such time, cannot be examined for the presence or absence of defects. FIG. 1 merely shows two flutes 3 in the periphery of each of the conveyors 1, 2; however it will be understood that each such conveyor is normally provided with a large number of equidistant axially parallel flutes each of which receives an article for transport along an elongated path having convex portions which are defined by drum-shaped conveyors. The cigarettes 4 are held in the respective flutes 3 by suction which is applied by way of suction ports machined into the conveyors 1 and 2 in a manner which is well known from the art of transporting cigarettes or the like and, therefore, is not specifically shown in the drawing. It suffices to say that each cigarette 4 is held in the respective flute 3 of the conveyor 1 during travel from a station where it is admitted into such flute and to the station (transfer zone) 6 where it is transferred from the reseptive flute of the conveyor 1 into the oncoming flute 3 of the conveyor 2. The manner in which the cigarettes 4 are attracted to the surfaces bounding the flutes 3 of the conveyor 2 is the same. The means for regulating the application of suction so that the cigarettes 4 are held only while they are supposed to share the movement of the respective conveyor can include stationary valve plates at the axial ends of the respective conveyors and means for drawing air from grooves which are machined into such valve plates and communicate with those flutes which are supposed to contain cigarettes 4. For example, the conveyor 1 of FIG. 1 can receive successive filter cigarettes 4 from a severing conveyor or from a turnaround device in a filter tipping machine of the type known as MAX or MAX S. Such machines are manufactured and sold by the assignee of the present application.

It will be noted that the conveyors 1 and 2 transport cigarettes 4 in a direction which is indicated by arcuate arrows and is normal to the axes of the cigarettes 4. The conveyor 1 is driven to rotate in a clockwise direction, and the conveyor 2 is driven to rotate in a counterclockwise direction, as viewed in FIG. 1. The peripheral speed of the conveyor 1 matches the peripheral speed of the conveyor 2.

FIG. 1 further shows that the cigarette 4 which is received in a flute 3 of the conveyor 1 exposes at least half of the exterior of its tubular wrapper which normally consists in part of cigarette paper and in part of the material of the aforementioned uniting band. When such cigarette enters a flute 3 of the conveyor 2, the previously concealed portion of the exterior of its wrapper becomes exposed so that, if one half of the exterior of the wrapper is tested for the presence or absence of defects on the conveyor 1 and the other half is tested for the presence or absence of defects on the conveyor 2, such repeated testing results in an examination of the quality or appearance of the entire exterior of each and every wrapper. The reference character 7 denotes in FIG. 1 a first testing station where each and every cigarette 4 is tested in order to ascertain the presence or absence of defects in the lower half of its wrapper, namely in the section 12 of the exterior of its wrapper. At the same time, the remaining section 12' of such exterior is concealed because it is received in the respective flute 3 of the conveyor 1.

When the cigarette 4 which has been tested at the station 7 reaches a second testing station 9 while in a flute 3 of the conveyor 2, the previously tested section 12 is concealed and the previously concealed section 12' is exposed. The testing apparatus further comprises a first scanning arrangement 8 including means for testing the sections 12 of the exterior of cigarettes 4 at the station 7, and a second scanning arrangement 8 at the testing station 9. The arrangements 8 are preferably identical and, therefore, FIG. 1 merely shows certain details of the scanning arrangement 8 at the first testing station 7.

The conveyors 1 and 2 of the transporting means shown in FIG. 1 are immediately adjacent to each other, i.e., the conveyor 1 delivers successive cigarettes 4 directly into successive flutes 3 of the conveyor 2 at the transfer station 6. However, it is equally possible to provide the second testing station 9 on a conveyor which follows the conveyor 2 as long as the number of transfer stations between the testing stations 7 and 9 is an odd number to thus ensure that the sections 12 which are exposed at the testing station 7 become concealed at the testing station 9 and the sections 12' which are concealed at the station 7 become exposed at the station 9. For example, the transporting means can comprise two additional rotary drum-shaped conveyors which follow the conveyor 2, as considered in the direction of sidewise transport of cigarettes 4, and the second testing station 9 is provided on the fourth conveyor. In such apparatus, the number of transfer stations between the testing stations 7 and 9 equals three. All that counts is to ensure that the transporting means is designed to expose at the second station those sections of the exterior of successive articles 4 which are concealed at the testing station 7. It is further within the purview of the invention to provide more than two testing stations if the nature of the transporting means is such that an examination of the entire exterior of each and every article is more satisfactory or more convenient if the number of testing stations exceeds two.

In the embodiment of FIG. 1, each of the scanning arrangements 8 comprises two identical mirror symmetrical scanning units 13 and 13'. The construction of each unit 13 of FIG. 1 is identical to that of the associated unit 13'; therefore, the constituents of the unit 13' are denoted by the same reference characters as those of the unit 13. Each of the units 13, 13' is an optical scanning unit. Therefore, each of these units comprises a light source 14 which emits light in a direction toward a lens 16 forming part of light conducting means for focusing light upon the respective half 12a or 12b of the exposed section 12 of the exterior of the cigarette 4 in the flute 3 which happens to be located at the testing station 7. Such light conducting means further comprises a partially transmitting mirror 17 which reflects a portion of light issuing from the respective source 14 through the aperture 11a of a suitable slotted diaphram 11 and toward the corresponding half 12a or 12b of the respective section 12 at the station 7. The beam of light which has passed through the slot 11a of the diaphram 11 thereupon passes through a light transmitting wall or pane 21 constituting a component of a protective enclosure for the optical system of the respective unit 13 so that the components of the optical system are not contaminated by dust and/or other solid matter or liquid matter in the region of the testing station 7. Each light source 14 can constitute a single elongated strip-shaped light source or it may consist of one, two or more rows of discrete round or otherwise configurated light sources. The light conducting means which is interposed between each source 14 and the exterior of the wrapper of the cigarette 4 at the testing station 7 is arranged to direct light against the respective portion 12a or 12b all the way from one end to the other end of the respective cigarette 4. The purpose of the diaphrams 11 is to prevent excessive straying of light which issues from one of the sources 14 onto the portion (12a or 12b) of the wrapper which is supposed to be illuminated by light issuing from the other of the two sources 14 shown in the lower part of FIG. 1.

Each of the scanning units 13 and 13' further comprises optoelectrical monitoring means 18 for the light beams which are reflected by the portions 12a, 12b of the section 12 of the article 4 at the testing station 7. Such units further comprise means (note the lenses 19) for focusing reflected light upon the constituents of the monitoring means 18. In the apparatus which is shown in FIG. 1, a portion of the path of light which issues from a source 14 and is directed toward the respective portion 12a or 12b of the section 12 of the exterior of the cigarette 4 at the testing station 7 coincides with a portion of the path for reflected light from the portion 12a or 12b toward the respective monitoring means 18. Such reflected light passes through the respective partially transmitting mirror 17 and is thereupon focused by the lens 19 upon the respective monitoring means 18. The feature of providing common path portions for incident and reflected light is desirable and advantageous because it ensures the establishment of particularly satisfactory reflection conditions.

Each of the partially transmitting mirrors 17 can be designed in such a way that it reflects the major part of incident light and transmits the remaining minor part of such light in a direction toward the respective portion 12a or 12b or toward the respective lens 19. If the mirror 17 reflects the major part of light which issues from the respective source 14, the major part of light issuing from such source is reflected back against the corresponding monitoring means 18. This enhances the sensitivity of the testing apparatus. The fact that a substantial precentage of radiation issuing from the corresponding source 14 is permitted to pass through the mirror 17 can be compensated for by utilizing high-intensity light sources.

Figure 3:
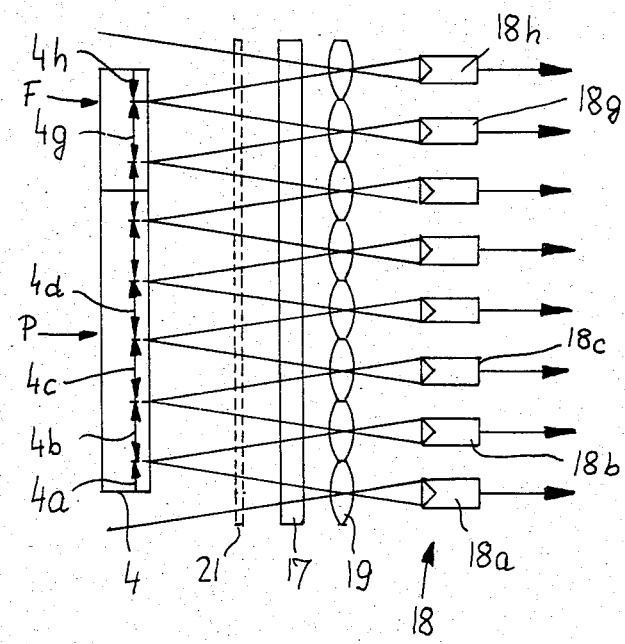
FIG. 3 is a schematic plan view of one unit of one of the two scanning means in the apparatus of FIG. 1.

FIG. 3 shows that each monitoring means 18 comprises a battery of optoelectrical transducer 18a, 18b . . . 18g, 18h. Each such transducer is arranged to ascertain the characteristics of radiation which is reflected by a relatively short part or increment of the respective portion 12a or 12b of the exposed section 12 at the testing station 7. Such relatively short increments of the exterior of the cigarette 4 are denoted by the characters 4a, 4b . . . 4g, 4h. The light conducting means which serves to focus reflected light upon the transducers 18a to 18h comprises a series of discrete lenses 19 which are disposed behind the partially transmitting mirror 17 and are separated from the path for the cigarettes 4 by the aforementioned light-transmitting wall or pane 21. The row of transducers 18a to 18h extends in parallelism with the axis of the cigarette 4 at the testing station 7, i.e., at right angles to the direction of travel of cigarettes 4 with the conveyor 1. If desired, the arrangement of optical elements forming part of the scanning unit 13 or 13' can be such that radiation which issues from the respective source 14 and is reflected by the exterior of the cigarette 4 at the testing station is monitored in part by two neighboring transducers of the monitoring means 18. This ensures that each and every increment of the portion 12a or 12b shown in FIG. 1 is invariably tested by at least one of the transducers. For example, the transducer 18b of FIG. 3 can be designed to ascertain the characteristics of light which is being reflected by the increment 4b as well as some light which is reflected by the neighboring increments 4a and 4c. Analogously, the transducer 18c can receive light from the increment 4c as well as some light from the neighboring increments 4b and 4d, and so forth. As mentioned above, this ensures that each and every increment of the exterior of each article 4 is tested not later than when such article advances beyond the second testing station 9.

The number of increments into which the portion 12a or 12b at the testing station 7 is divided depends on the number of transducers which form part of the respective monitoring means 18 and the desired resolution capability and sensitivity of the testing apparatus.

Figure 2:
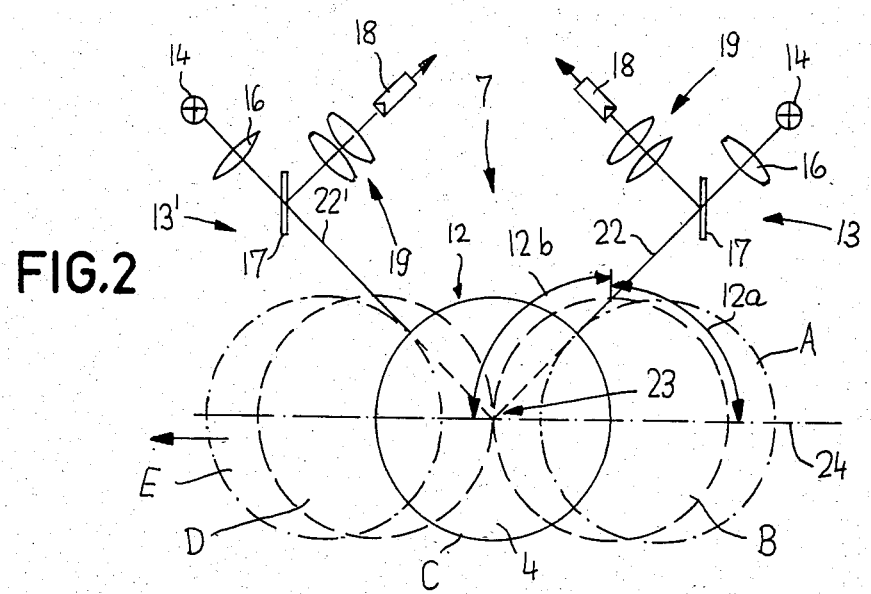
FIG. 2 is a greatly enlarged end elevational view of a cigarette in several positions during testing in an apparatus of the type shown in FIG. 1.

FIG. 2 illustrates the manner in which the section 12 of the exterior of a cigarette 4 at the testing station 7 is examined by the units 13 and 13' of the corresponding scanning arrangement 8. The construction of each of the scanning units 13, 13' shown in FIG. 2 is the same as the construction of the similarly referenced scanning units in FIG. 1 except that each of the light conducting means 19 comprises several optical elements. Each of the two monitoring means 18 again comprises at least one row of discrete optoelectrical transducers, such as the transducers 18a to 18h of FIG. 3. The path of radiation issuing from the right-hand source 14 is indicated by the line 22, and the path of radiation issuing from the left-hand source 14 is indicated at 22'. The lines 22 and 22' intersect each other in a plane 24 which includes the axes of cigarettes 4 on the conveyors 1 and 2 of the transporting means. For the sake of simplicity, the line 24 denoting the common plane of the axes of cigarettes 4 on the conveyors 1 and 2 is a straight line. Actually, and if the transporting means comprises rotary drum-shaped conveyors (such as the conveyors 1 and 2 of FIG. 1), the plane including the axes of cigarettes 4 is a partially concave and partially convex plane with radii of curvature corresponding to the radii of the peripheral surfaces of conveyors 1 and 2.

FIG. 2 shows a presently preferred mounting and mutual positioning of the components of the scanning units 13 and 13' at the testing station 7. Thus, the path 22 makes an angle of 90° with the path 22', such paths intersect each other in the plane 24, and each of the paths 22, 22' makes an angle of 45° with the plane 24. The line where the paths 22, 22' intersect each other is shown at 23. As mentioned above, such line is located in the plane 24. It should be borne in mind that each of the paths 22, 22' is relatively wide, as considered at right angles to the plane of FIG. 2, namely the width of each such path at least equals the axial length of a cigarette 4.

The just mentioned mutual inclination of the paths 22, 22' and the inclination of such paths relative to the plane 24, which is common to the axes of cigarettes 4 on the conveyors 1 and 2, ensures that when a cigarette 4 is located exactly at the testing station 7, the area of the portion 12a equals the area of the portion 12b. The portions 12a and 12b together constitute the section 12 which may be slightly larger than half the exterior of the wrapper of the cigarette 4 at the testing station 7. This ensures that the scanning arrangement 8 at the testing station 7 can ascertain the characteristics of radiation which is reflected by a little more than half the exterior of the cigarette at such station. Since the scanning arrangement 8 at the testing station 9 also examines more than half the exterior of the wrapper of the cigarette 4 at the station 9, such division of the tasks of the two scanning arrangements 8 invariably ensures that each and every portion of the exterior of each and every cigarette 4 has been adequately tested upon completion of the testing operation at the station 9. In addition, this ensures that the scanning arrangement 8 at the station 7 or 9 need not examine the exterior of a wrapper all the way to the periphery of the respective conveyor 1 or 2 because light which impinges upon the exterior of the cigarette 4 at the station 7 or 9 very close to the periphery of the respective conveyor progresses substantially tangentially of the respective cigarette so that reflection of such light is not as satisfactory as the reflection of light which impinges upon the remaining portion of the exposed section 12 or 12'. In other words, the exposure of a little more than half the exterior of the cigarette 4 at each of the testing stations 7 and 9 ensures that the scanning units 13 and 13' must only ascertain the presence or absence of defects in those portions of the exterior of the respective cigarette which adequately reflects light so that the reflected light can be properly evaluated by the corresponding row of transducers 18a to 18h. Such arrangement ensures that the monitoring action is highly reliable, i.e., that the transducers transmit signals which accurately reflect the condition of the corresponding increments of the section 12 or 12' of the cigarette 4 at the station 7 or 9.

Referring again to FIG. 2, when an oncoming cigarette 4 reaches the phantom-line position A, it is about to enter the testing station 7. The cigarette 4 is assumed to advance in a direction from the right to the left, as viewed in FIG. 2. The scanning units 13 and 13' of the arrangement 8 shown in FIG. 2 are expected to ascertain the presence or absence of defects in that section (12) of the exterior of the cigarette 4 at the station 7 which is located above the plane 24, as viewed in FIG. 2. In other words, at least the major part of the remaining (lower) section (12') of the cigarette shown in FIG.

2 is assumed to be surrounded by the surface bounding the corresponding flute 3 of the conveyor 1.

In the position A, the corresponding section 12 of the exterior of the wrapper of the cigarette 4 is about to enter into the path (line 22) of light which issues from the source 14 of the scanning unit 13. As the cigarette 4 advances from the position A toward the broken-line position B, its exterior begins to reflect light and such reflected light propagates itself in part along the path 22 to be thereupon reflected by the mirror 17 and focused by the optical elements 19 upon the corresponding row of transducers 18a to 18h constituting the monitoring means 18 of the scanning unit 13. If all of the transducers 18a to 18h of the monitoring means 18 in the scanning unit 13 begin to receive reflected light at the same time, this indicates that the cigarette 4 advancing beyond the position A and toward the position B has a desirable circular cylindrical configuration and that it is not bent. This will be readily appreciated since, if the cigarette 4 were flexed so that its axis would not extend exactly at right angles to the plane of FIG. 2, some of the transducers 18a to 18h of the monitoring means 18 in the scanning unit 13 would receive reflected light ahead of the remaining transducers. If the deviation in timing of impingement of reflected light upon all of the transducers 18a to 18h is sufficient, the evaluating circuit which is connected with the monitoring means 18 of the scanning unit 13 generates a "defect" signal which is utilized to segregate the respective cigarette 4 from the remaining cigarettes.

When the cigarette 4 reaches the position B of FIG. 2, the entire portion 12a of the section 12 is in a position to reflect light issuing from the source 14 of the scanning unit 13. In other words, the transducers 18a to 18h of the monitoring means 18 in the scanning unit 13 then generate signals which can be evaluated in order to ascertain whether or not the portion 12a contains any defects such as holes, specks of dirt, remnants of adhesive, open seams, frayed ends or the like. The cigarette 4 enters the path 22' of light issuing from the light course 14 of the scanning unit 13' of FIG. 2 not later than when it begins to leave the position B. Light which issues from the source 14 of the scanning unit 13' is then reflected by the portion 12b of the section 12 of the cigarette 4, and such reflected light is directed and focused upon the transducers 18a to 18h of the monitoring means 18 in the scanning unit 13'.

The solid-line position C of the cigarette 4 in FIG. 2 corresponds to the position of the cigarette 4 shown at the transfer station 7 in FIG. 1. When the cigarette 4 reaches the position C, reflection of light which issues from the two sources 14 shown in FIG. 2 takes place substantially at right angles to the corresponding portion of the exterior of the cigarette 4 so that the paths of emitted and reflected light (lines 22 and 22') coincide in the regions between the respective mirrors 17 and the line 23 of intersection between the paths 22 and 22'. At such time, the ability of the section 12 to reflect light which is emitted by the two sources 14 is most pronounced.

When the cigarette 4 of FIG. 2 reaches the position D, it begins to leave the path 22. Furthermore, the portion 12b of the section 12 begins to leave the path 22'. The cigarette 4 begins to advance beyond the testing station 7 when it leaves the phantom-line position E on its way toward the transfer station 6 of FIG. 1. If the cigarette 4 is a true cylinder and does not exhibit any dents, nicks or similar deformities, all of the transducers 18a to 18h of the monitoring means 18 forming part of the scanning unit 12' of FIG. 2 cease to receive light at the same time. If this is not the case, the evaluating circuit which receives signals from the transducers 18a to 18h of the monitoring means 18 in the scanning unit 13' can generate a "defect" signal which is used to segregate the respective cigarette 4 from other cigarettes. The arrangement is preferably such that the evaluating circuit effects an ejection of the tested cigarette 4 only if its configuration departs sufficiently from an ideal configuration so that the segregation is warranted. In other words, minor depressions or minor departures of the outline of the cigarette 4 from normal (e.g., minor flexure or bending or minor nicking) should not entail a segregation of such cigarette from the remaining cigarettes.

The portions 12a and 12b of the section 12 of the exterior of the cigarette 4 shown in FIG. 2 can partially overlap so as to ensure that the apex of the exterior of the cigarette (at the 12 o'clock position as viewed in FIG. 2) is fully examined for the presence or absence of defects before the cigarette leaves the testing station 7.

The testing of successive cigarettes 4 at the second testing station 9 of FIG. 1 is identical with the testing described in connection with FIG. 2, except that the units 13 and 13' of the corresponding scanning arrangement 8 examine radiation which is reflected by the previously concealed section 12' of the exterior of the respective cigarette 4.

An important advantage of the apparatus which is shown in FIGS. 1, 2 and 3 is that it reliably examines radiation which is reflected by each and every portion of the exterior of each and every cigarette 4. This is due to the provision of several testing stations as well as to the provision of several monitoring or scanning units (13, 13') at each of the testing stations. The aforediscussed mutual inclination of radiation issuing from the sources 14 in each of the two scanning means 8 also contributes to reliable scanning of the entire exterior of each cigarette. Moreover, the aforementioned orientation of radiation sources and light conducting means in each of the scanning arrangements 8 ensures that the exterior of each cigarette 4 is tested under identical or practically identical circumstances for each and every portion and section of such exterior. This also contributes to more reliable detection of defects which warrant segregation of corresponding cigarettes from the remaining (satisfactory) cigarettes. The absence of need for reliance on reflection of light which impinges substantially tangentially upon the exterior of a cigarette at the station 7 or 9 also contributes to more reliable testing of such articles. As mentioned above, dispensal with reliance upon radiation which cannot be adequately reflected by the exterior of a cigarette is possible at least in part because the flutes 3 of the conveyors 1 and 2 need not expose only 50 percent but preferably expose at least slightly more than 50 percent of the exterior of cigarettes 4 on the respective conveyors.

The provision of monitoring means 18 each of which includes a substantial number of discrete transducers (such as 18a to 18hcontributes to more satisfactory local resolution of the testing apparatus. The provision of optical light conducting elements is desirable and advantageous because they ensure proper coherence of emitted beams of radiation as well as of reflected radiation and adequate focusing of emitted radiation upon the corresponding portions of the exterior of a cigarette at the testing station 7 or 9 as well as adequate focusing of reflected radiation upon the corresponding transducers of the monitoring means 18. Moreover, the provision of suitable optical light conducting elements (16, 17, 19) contributes to compactness of the testing apparatus.

Light which issues from sources 14 in each of the scanning arrangements 8 can be said to constitute a curtain of radiation which is relatively thin and extends along the full length of the cigarette approaching and passing through the testing station 7 or 9. Such curtains intersect successive portions of the section 12 or 12' of the cigarette at the station 7 or 9 so that the testing apparatus ensures a more or less linear scanning of successive increments of the exterior of each cigarette 4. Such scanning takes place from the one to the other axial end of the cigarette at the station 7 or 9. Linear scanning of the sections 12 and 12' ensures highly reliable detection of all kinds of defects which the improved testing apparatus is to uncover in order to enable the associated evaluating means to decide whether or not the corresponding cigarette warrants segregation from the remaining cigarettes.

Figure 4:
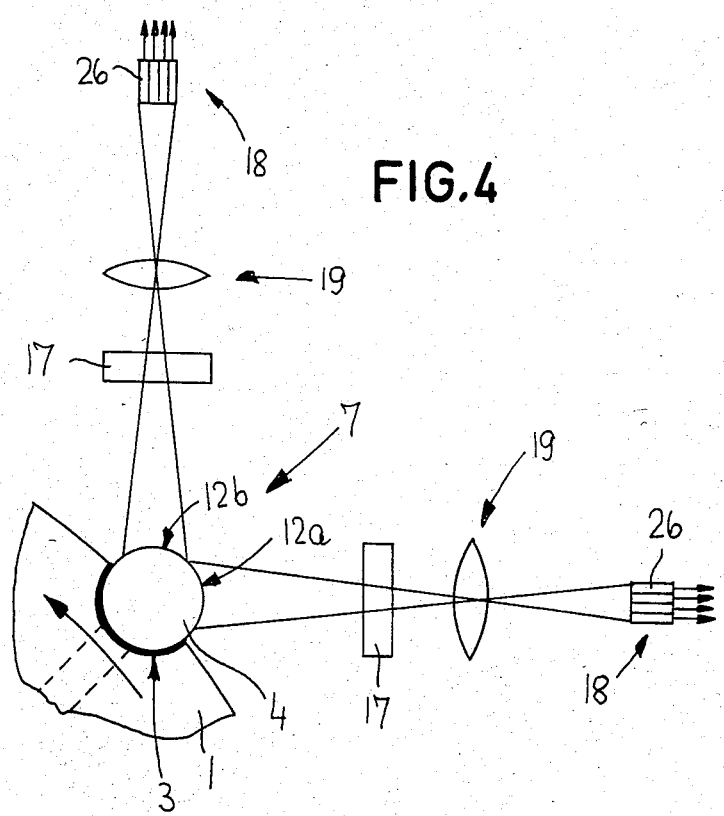
FIG. 4 is a fragmentary end elevational view of a modified testing apparatus.

FIG. 4 illustrates a portion of a modified testing apparatus. All such parts which are identical with or clearly analogous to the corresponding parts of the apparatus of FIGS. 1 to 3 are denoted by the same reference characters. FIG. 4 merely shows one (namely the drum 1) of the conveyors which together constitute the transporting means of the apparatus. The conveyor 1 is assumed to rotate in a counterclockwise direction, as viewed in FIG. 4. The scanning arrangement at the testing station 7 again comprises two scanning units which are mirror symmetrical to each other with reference to a plane that is normal to the plane of FIG. 4 and includes the axis of the conveyor 1 and of the cigarette 4 at the testing station 7.

The radiation source or sources of the scanning arrangement of FIG. 4 are not specifically shown. It suffices to say that such source or sources direct light against the exposed section of the exterior of the cigarette 4 at the testing station 7 and the reflected light passes through optical elements 17 and 19 on its way toward the corresponding monitoring means 18. In accordance with a feature of the invention, each of the monitoring means 18 comprises a two-dimensional array 26 of transducers 27 (see FIG. 5A) which together form a raster capable of receiving the reflected image 28 of the entire cigarette 4 at the testing station 7. The transducers 27 form two groups of parallel rows and the rows of one group are disposed at right angles to the rows of the other group.

Figure 5A:
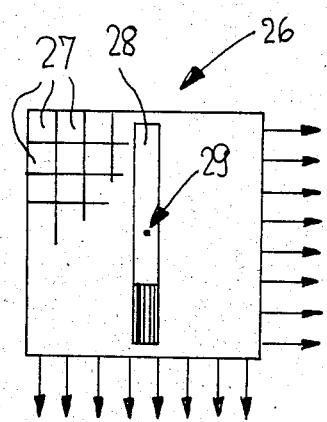
FIG. 5A is an enlarged plan view of a two-dimensional array of transducers in the testing apparatus of FIG. 4.

If the optical elements 19 shown in FIG. 9 are spherical lenses, one for each of the transducers 27 shown in FIG. 5A, the proportions of the image 28 of the cigarette 4 on the two-dimensional array 26 of transducers 27 are the same as that of the cigarette. Consequently, if the wrapper of such cigarette exhibits a circular hole 29 (see FIG. 5A), the image of such defect is a small dot in the imate 29. The corresponding transducer 27 then transmits to the evaluating circuit a weaker or stronger signal to ensure that the latter effects a segregation of the cigarette 4 which exhibits such defect.

Figure 5B:
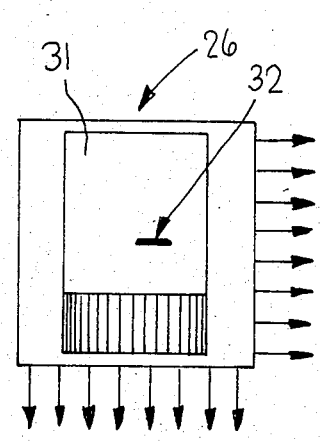
FIG. 5B is a similar plan view but showing the manner in which the image of an article on the array is distorted by appropriate selection of means for focusing reflected radiation upon the transducers.

However, if the spherical lenses are replaced with cylindrical lenses which focus reflected radiation upon the transducers 27 of the two dimensional array 26 shown in FIGS. 5A and 5B, (in other words, if the spherical lenses 19 are replaced with cylindrical lenses) the image 31 on the array 26 of transducers 27 is distorted in at least one direction as can be readily ascertained by comparing the images 31 and 28. Consequently, the dot 29 of FIG. 5A is converted into an elongated line 32 which can be more readily detected or sensed by the corresponding transducer or transducers to furnish a more reliably indication for segregation of the respective cigarette 4 from the remaining cigarettes. The orientation of cylindrical lenses which generate the image 31 of FIG. 5B is such that they create an image having a width which is much greater than the width of the image 28 shown in FIG. 5A. Of course, it is also possible to distort the image in a different direction or in several directions so as to further facilitate detection of defects which may be present in the scanned section of the exterior of the cigarette at the testing station 7 of FIG. 4. The scanning arrangement at the other of the two testing stations in the apparatus including the structure of FIG. 4 is preferably the same as the illustrated scanning arrangement. It will be noted that the utilization of cylinder lenses as a means, or as components of means, for focusing reflected radiation upon two-dimensional arrays of transducers 27 further enhances the sensitivity of the testing apparatus.

The apparatus of FIGS. 4, 5A and 5B can further comprise means for scanning the image 28 or 31 line by line so as to detect the presence of a defect 29 or 32 and to effect the generation of a "defect" signal which is utilized for segregation of the respective cigarette from the remaining cigarettes.

Figure 6:
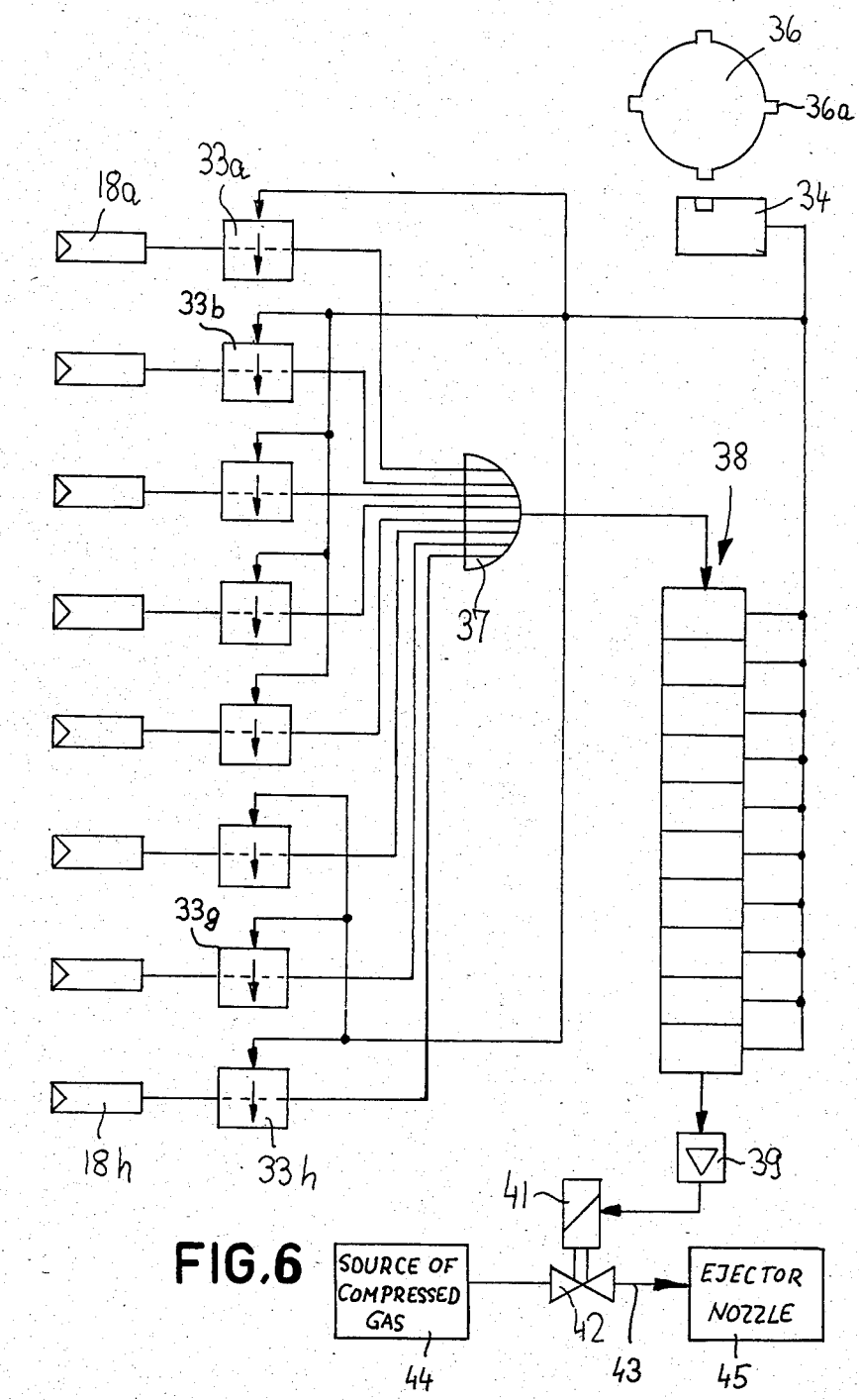
FIG. 6 is a diagrammatic view of an evaluating circuit which receives signals from the transducers of one unit in one of the scanning means forming part of the improved apparatus.

FIG. 6 is a simplified diagram of an evaluating circuit which can be utilized with a row of transducers 18a to 18h. The outputs of the transducers 18a to 18h are connected with the first inputs of corresponding threshold circuits 33a, 33b . . . 33g, 33h, one for each of the transducers. The threshold circuits have second inputs connected to a common pulse generator 34 in the form of a proximity detector serving to generate a pulse whenever it is approached by a protuberance 36a of a rotating timing disc 36 which is driven at the speed of the conveyors 1, 2 or at a proportional speed so that the threshold circuits 33a to 33h receive pulses whenever a cigarette 4 is located at the testing station 7 or 9, depending upon whether the transducers 18a to 18h of FIG. 6 form part of the monitoring means 18 in the scanning arrangement 8 at the testing station 7 or 9. The outputs of the threshold circuits 33a to 33h are connected to the corresponding inputs of a common OR gate 37 the output of which is connected to the first stage of a shift register 38. The stages of the shift register 38 also receive pulses from the pulse generator 34. The output of the last stage of the shift register 38 transmits signals to an amplifier 39 which, in turn, transmits signals to the solenoid 41 of a valve 42 installed in a conduit 43 which can admit compressed air from a source 44 to an ejector nozzle 45 serving to expel defective cigarettes 4 from the path which is defined by the conveyor 2 or by a conveyor which follows the conveyor 2.

The threshold circuits 33a to 33h transmit signals to the OR gate 37 whenever the intensity of signals which are furnished by the respective transducers 18a to 18h exceeds or drops below a preselected threshold value. Such signals are indicative of the presence or absence of defects in the corresponding portions of the exterior of the cigarette 4 at the testing station 7 or 9. The purpose of the shift register 38 is to transport "defect" signals in imitation of the transport of the corresponding articles 4 toward the ejecting station (nozzle 45). This ensures that the nozzle 45 invariably effects ejection of a defective cigarette 4, namely a cigarette which has been found to be defective during examination at the testing station 7 or 9.

If desired, the evaluating circuit of FIG. 6 can comprise additional threshold circuits which are connected with the transducers of the other scanning units forming part of the improved testing apparatus. However it is equally possible to provide a discrete evaluating circuit for each of the various scanning units. This allows for convenient discrimination between defects which are detected in different portions of the exterior of cigarettes 4.

An important advantage of the improved method and apparatus is that they allow for complete optical scanning of discrete rod-shaped articles of the tobacco processing industry subsequent to segregation of such articles from a continuous rod. Furthermore, the improved apparatus is capable of treating the articles gently because such articles need not rotate about their respective axes at the testing station 7 or 9. In fact, the provision of several testing stations is attributable to the fact that the improved apparatus need not include any means for rotating the articles about their axes.

Another important advantage of the improved apparatus is that it is compact and can be readily installed in existing production lines for filter cigarettes or other rod-shaped smokers' articles.

An additional important advantage of the improved apparatus is that it can furnish "defect" signals in response to detection of a wide variety of defects including holes, open seams, frayed ends, specks of dirt, spots of adhesive, absence or improper application of imprints, flexing, bending or denting of the articles, improper orientation of filter plugs or plain cigarettes, folds in the tipping paper which connects filter plugs to plain cigarettes, outwardly extending portions of tipping paper and bent corner portions of tipping paper. The testing operation is carried out while the articles advance sideways at the speed which is customary in a modern production line so that the testing of articles in accordance with the present invention does not necessitate a slow-down of operation of such production lines.

A further important advantage of the improved apparatus is that it can examine, with the same degree Aof accuracy, the condition or quality of each and every portion of the entire exterior of each rod-shaped article.

Still another important advantage of the improved apparatus is its pronounced versatility. In other words, and as already mentioned above, the improved apparatus is capable of detecting and generating defect signals in response to detection of a wide variety of defects. The defects include defects of the exterior proper, such as holes which appear as dark spots and specks of dirt or dust which cause similar reaction in response to illumination by light or other types of radiation. The same applies for the monitoring of imprints (which denote the name, tradename or other information pertaining to the manufacturer or to the product) as well as remnants of adhesive (which normally reflects more light than the material in a hole or within an open same). In addition to such defects, the apparatus can also ascertain whether or not the outline of each article is a true cylinder and/or whether such outline departs from a true cylinder sufficiently to warrant segregation. As mentioned above, such departure can include bending, flexing, the presence of dents or nicks in the articles which are being tested and a combination of such deformities.

Still further (and this is important in connection with the testing of filter cigarettes, cigars or cigarillos), the improved apparatus can be utilized for detection of defects pertaining to the applied tipping paper, namely whether or not the tipping paper is properly convoluted around the filter plugs and the adjacent end portions of plain cigarettes, cigars or cigarillos, as well as whether or not the tipping paper includes portions which extend outwardly beyond the general outline of the respective article.

It will further be appreciated that visible light constitutes but one form of radiation which can be resorted to in connection with the testing in accordance with the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for ascertaining the presence of defects at the exterior of rod-shaped articles of the tobacco processing industry, comprising means for transporting a series of articles in a predetermined direction, at right angles to the axes of the articles, and along successive portions of a predetermined path in each of which a different section of the exterior of the articles is exposed, said transporting means comprising several neighboring conveyors with a transfer zone between neighboring conveyors, said conveyors including first and second conveyors and said portions of said path including first and second portions which are defined by the respective conveyors, the number of transfer zones in said transporting means between said first and second conveyors being an odd number and said conveyors including means for holding the articles against movement with reference to the respective conveyors during transport along the respective portions of said path; and discrete scanning means for each portion of said path, each of said scanning means comprising means for monitoring the respective section of the exterior of the article in the corresponding portion of said path and for generating signals in response to detection of defects.

2. The apparatus of claim 1, wherein said transporting means includes means for conveying said series of articles in the form of a single layer.

3. The apparatus of claim 1, wherein each of said scanning means comprises at least one optical scanning unit.

4. The apparatus of claim 3, wherein each of said units includes a source of radiation, means for directing radiation from said source against the respective section of the exterior of the article in the corresponding portion of said path whereby the characteristics of such radiation change in response to impingement upon a defective section of the exterior of the article in the corresponding portion of said path, and means for monitoring such changes in the characteristics of said radiation.

5. The apparatus of claim 4, wherein each of said sources is a light source and said monitoring means include optoelectrical transducer means.

6. The apparatus of claim 4, wherein each of said sections extends along the full length of the respective article and the monitoring means of each of said units includes a plurality of discrete transducers each arranged to detect changes in the characteristics of radiation upon impingement upon one of several longitudinally spaced increments of the respective section of the exterior of the article in the corresponding portion of said path.

7. The apparatus of claim 6, wherein each of said transducers is an optoelectrical transducer arranged to ascertain the characteristics of radiation which is reflected by the respective increment of the exterior of the article in the corresponding portion of said path.

8. The apparatus of claim 1, wherein each of said scanning means comprises several optical scanning units having sources of radiation and radiation conducting means for directing radiation issuing from said sources against the respective section of the exterior of the article in the corresponding portion of said path at a different angle to said path.

9. The apparatus of claim 8, wherein each of said radiation conducting means is arranged to direct radiation against the respective section of the exterior of the article in the corresponding portion of said path and along the full length of such article.

10. The apparatus of claim 8, wherein each of said scanning means comprises a pair of units and the radiation conducting means of each pair of units are arranged to direct radiation at an angle of approximately 90° to each other.

11. The apparatus of claim 10, wherein the axes of the articles in said path are disposed in a predetermined plane and the radiation directing means of each of said pairs of units are arranged to direct beams of radiation at angles of approximately 45° to said plane.

12. The apparatus of claim 11, wherein the radiation beams which are directed by the radiation directing means of each of said pairs of units intersect each other in said plane.

13. The apparatus of claim 1, wherein each of said scanning means comprises at least one elongated radiation source extending at right angles to said direction and in at least substantial parallelism with the articles in said path.

14. The apparatus of claim 1, wherein each of said scanning means comprises at least one radiation source, first radiation conducting means for focusing radiation issuing from the source upon the respective section of the exterior of the article in the corresponding portion of said path whereby such section reflects radiation, transducer means arranged to monitor the characteristics of reflected radiation, and second radiation conducting means for focusing reflected radiation upon said transducer means.

15. The apparatus of claim 14, wherein said radiation conducting means comprise optical elements.

16. The apparatus of claim 15, wherein the transducer means of each of said scanning means comprises a battery of transducers and said second radiation conducting means of each of said scanning means comprises means for directing a different portion of reflected radiation against each of said transducers so that each transducer ascertains the characteristics of radiation which is reflected by one of several longitudinally spaced increments of the respective section of the exterior of the article in the corresponding portion of said path.

17. The apparatus of claim 14, wherein the radiation conducting means of each of said scanning means comprise mirrors and lenses arranged to provide for emitted and reflected radiation paths which include a common portion.

18. The apparatus of claim 1, wherein each of said scanning means includes at least one source of radiation and means for directing radiation from said source against the respective section of the exterior of the article in the corresponding portion of said path whereby such section reflects radiation and changes, if any, in the characteristics of reflected radiation are indicative of the presence of defects at the exterior of the corresponding article, and means for monitoring the characteristics of reflected radiation including a two-dimensional array of transducers located in the path of propagation of reflected radiation so that the radiation impinging upon such array forms an image of the corresponding article.

19. The apparatus of claim 18, wherein each of said scanning means further comprises radiation conducting means disposed in the path of propagation of reflected radiation and arranged to alter at least one dimension of the image which is formed on the respective array.

20. The apparatus of claim 1, wherein each of said scanning means comprises at least one light source, first light conducting means for focusing light which issues from the source upon the respective section of the exterior of the article in the corresponding portion of said path whereby the section reflects the thus focused light and changes, if any, in the characteristics of reflected light are indicatve of defects at the exterior of the corresponding article, optoelectrical transducer means for monitoring the characteristics of reflected light, and second light conducting means for focusing reflected light upon said transducer means, each of said second light conducting means comprising at least one cylinder lens.

21. The apparatus of claim 1, wherein each of said scanning means comprises a source of radiation, means for directing radiation upon the respective section of the exterior of the article in the corresponding portion of said path so that the section reflects such radiation and changes, if any, in the characteristics of reflected radiation are indicative of defects at the exterior of the corresponding article, means for monitoring the characteristics o radiation are indicative of defects at the exterior of the corresponding article, means for monitoring the characteristics of reflected radiation including a plurality of transducers arranged to generate signals denoting the characteristics of reflected radiation, and common evaluating means for signals which are transmitted by said transducers.

22. The apparatus of claim 21, wherein said evaluating means includes means for comparing the signals from the transducers with threshold signals and for generating "defect" signals when the differences between the characteristics of signals from said transducers and said threshold signals exceed preselected values.

23. A method of testing the exterior of elongated rod-shaped articles of the tobacco processing industry, comprising the steps of transporting a series of successive articles sideways along a predetermined path including a first portion wherein a first section of the exterior of each article is exposed at least substantially from end to end and a second portion wherein a different second section of the exterior of each article is exposed at least substantially from end to end; scanning the first sections of the exterior of successive articles in the first portion of said path for the presence of defects; scanning the second sections of the exterior of successive articles in the second portion of said path for the presence of defects; and holding the articles against rotation about their respective longitudinal axes in the course of said scanning steps.

24. The method of claim 23, wherein each of said scanning steps includes directing beams of radiation against the respective sections of the exterior of the article in the corresponding portion of said path whereby the exterior of the article reflects the radiation and the characteristics of reflected radiation are indicative of defects, if any, in the respective sections, and monitoring the characteristics of reflected radiation.

* * * * *